Figures 4, 5:
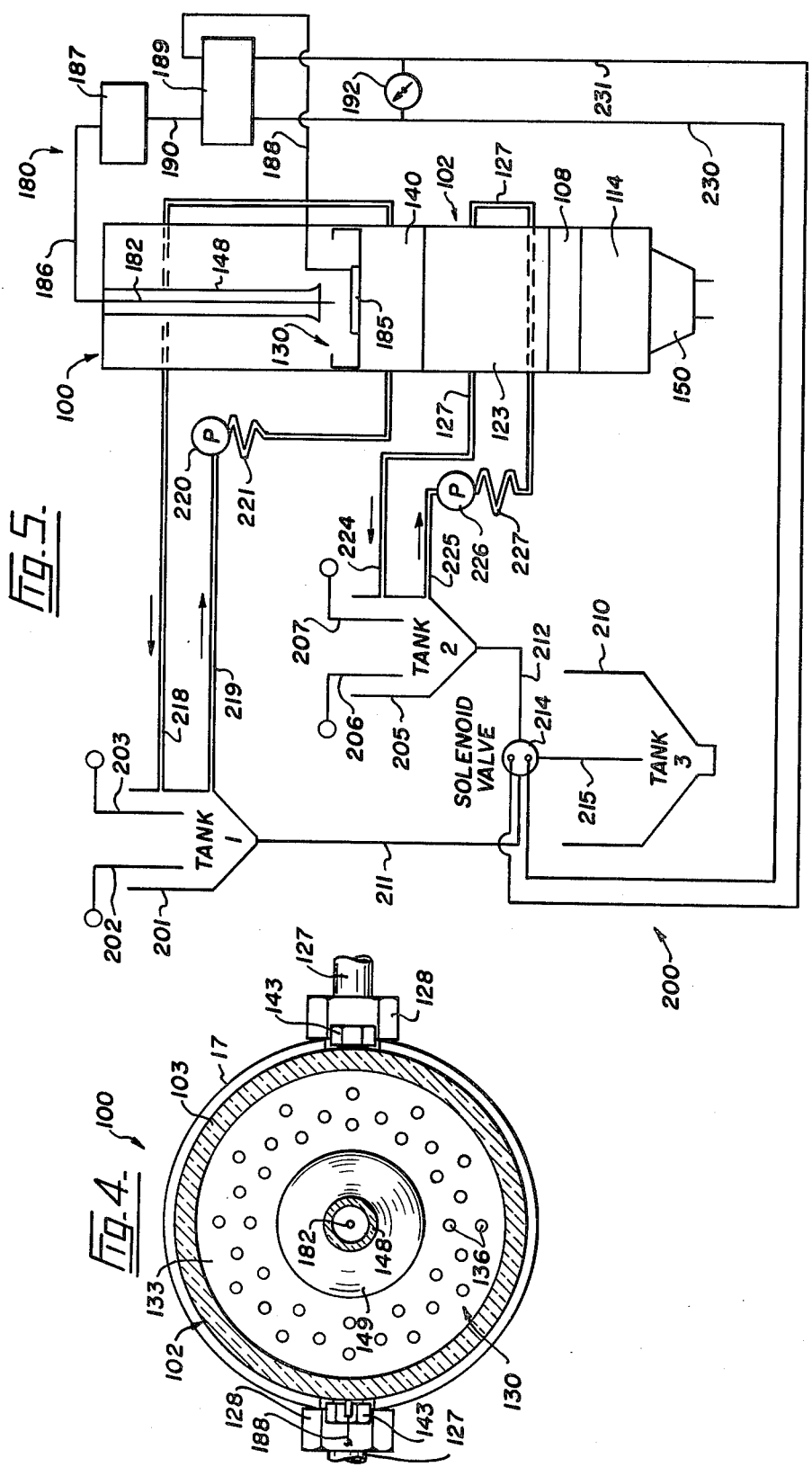

United States Patent [19]

Koblanski

[11] 4,179,937
[45] Dec. 25, 1979

[54] SOUND MEASURING DEVICE

[75] Inventor: John N. Koblanski, Burnaby, Canada

[73] Assignee: Ocean Ecology Ltd., Edmonton, Canada

[21] Appl. No.: 912,112

[22] Filed: Jun. 2, 1978

[51] Int. Cl.² ............................................. G01H 3/10
[52] U.S. Cl. ..................................................... 73/646
[58] Field of Search ................ 73/606, 645, 646, 647, 73/648, 1 DV, 53, 61.1 R

[56] References Cited

U.S. PATENT DOCUMENTS

| | | | |
|---|---|---|---|
| 2,055,713 | 9/1936 | Alder | 73/646 |
| 2,827,978 | 3/1958 | Henry | 73/646 |
| 2,832,214 | 4/1958 | Trommler | 73/606 |
| 3,572,088 | 3/1971 | Gericke et al. | 73/606 |
| 4,099,417 | 7/1978 | Shwartzman | 73/606 |

Primary Examiner—Charles A. Ruehl
Attorney, Agent, or Firm—Townsend and Townsend

[57] ABSTRACT

An instrument for measuring the intensity of sound waves has a container partly filled with liquid. An open-ended tube is supported by the container above the liquid. Below the container a clamping arrangement serves to hold a sound-producing device in acoustical contact with a bottom closure of the container. A sound lens carried by the container above the bottom closure concentrates sound waves generated by the device at a focal region located below the surface of the liquid and in vertical alignment with the tube. The resulting column of liquid is supporting by the tube and the column height is measured on a scale to indicate sound intensity.

10 Claims, 5 Drawing Figures

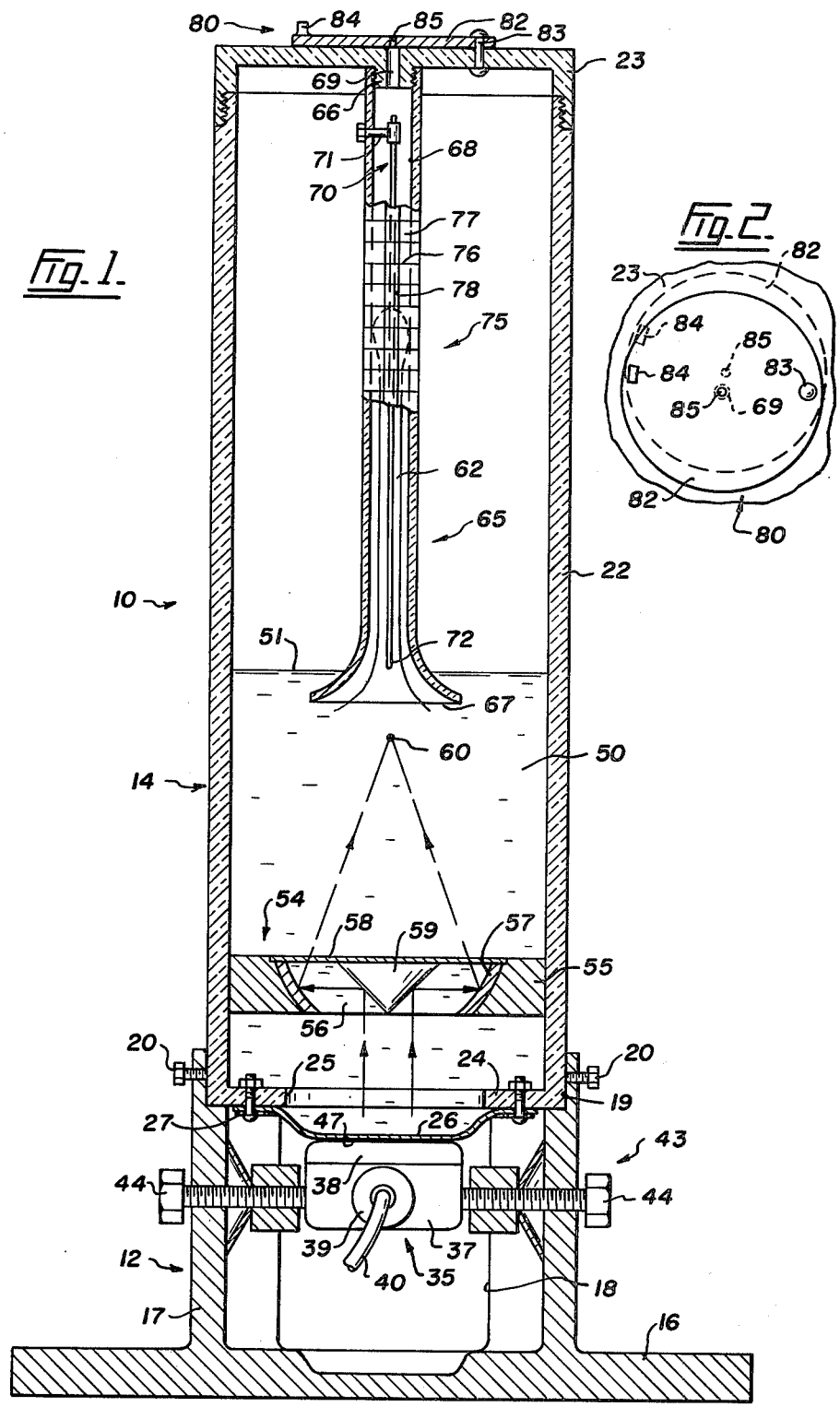

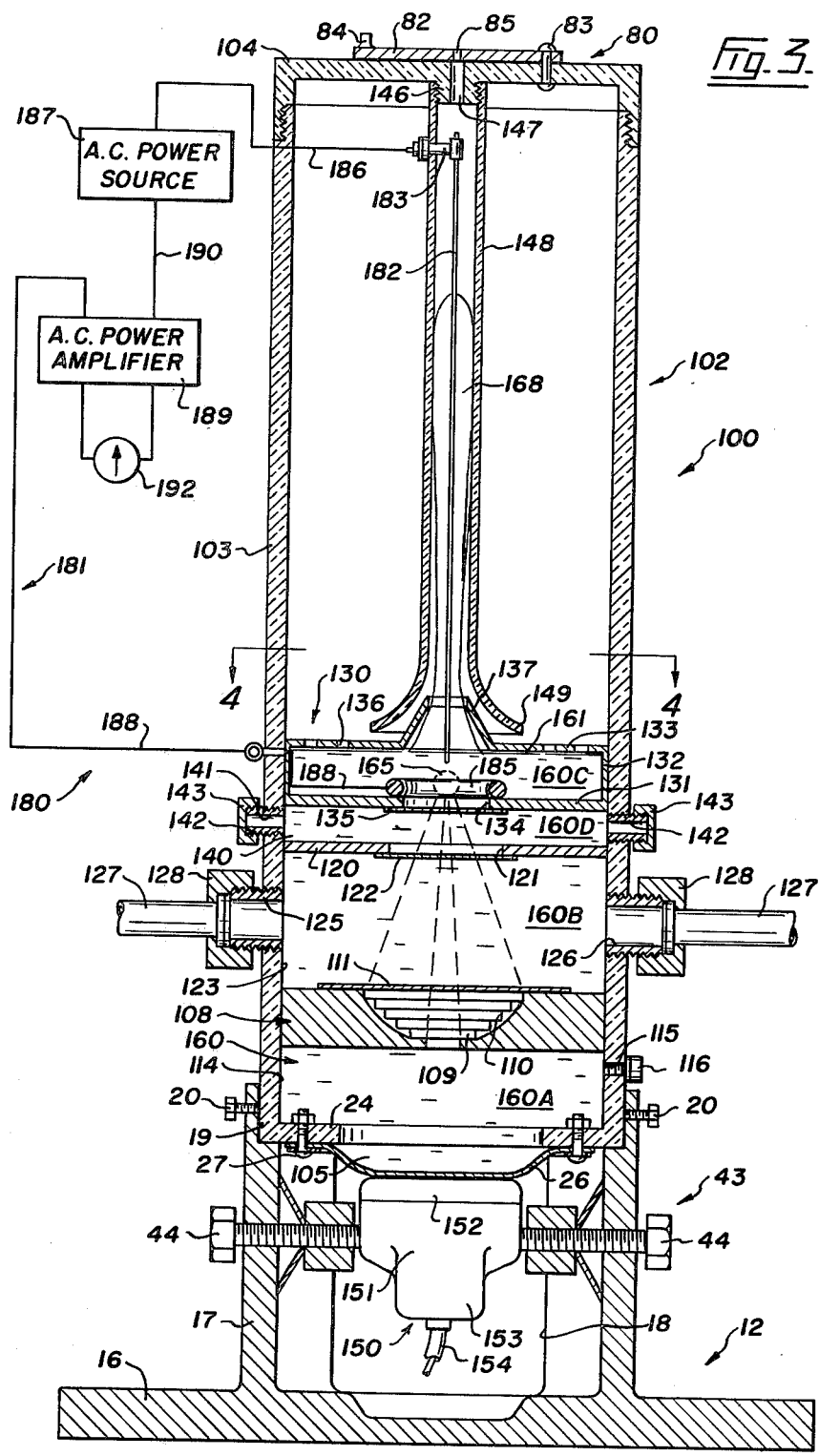

SOUND MEASURING DEVICE

This invention relates to apparatus for measuring the amplitude of sound waves.

It is difficult to provide an accurate measurement of the output of an acoustic wave generator particularly when ultrasonics are involved. The vibrational energy produced by an ultrasonic transducer for example, cannot readily be measured without the use of rather complex equipment which is best operated by an experienced technician. A known device for determining the acoustic radiation force of a piezoelectric crystal transducer is described in U.S. Pat. No. 2,827,978 which issued on Mar. 25, 1958 to G. E. Henry. Another known apparatus is covered by U.S. Pat. No. 2,874,794 issued on Feb. 24, 1959 to E. F. Kierman. These patented devices as well as other related instruments rely heavily on the skill of the user and otherwise are not too accurate or reliable. One reason for this is that any instrument using the radiation pressure phenomena to measure sound must utilize some form of beam balance to measure sound and this involves a delicate precision instrument which is not too reliable if handled roughly. There are other instruments for measuring the percentage constituents in a liquid by measuring the speed of sound in that liquid but these instruments are complex and expensive as well requiring the use of computers.

The present invention provides an improved method and means for determining the output of an ultrasonic transducer by utilizing the very intense energy which can be concentrated at a predetermined point when a beam of sound is properly focused. It is known that when the focal point is located below the surface of a body of liquid, the resulting radiation pressure is great enough to cause a fountain of the liquid to spurt above the liquid surface. This phenomonon forms the basis of U.S. Pat. No. 4,032,438 dated June 28, 1977, the inventor being John N. K. Koblanski. The height of the spurt of liquid, if it is sustained and properly constrained laterally, can be measured and related to the energy output of the transducer and this invention provides means for doing so. Furthermore, the invention provides additional means for flowing a test liquid through the focused sound beam so that the measurement obtained will differ from a reference reading according to the impedance factor of the test liquid and this revised measurement can be utilized to control a system which is producing the test liquid. Both embodiments of the invention are simply and inexpensively constructed and can readily be operated even by relatively inexperienced workmen.

More specifically, apparatus according to the present invention can be defined as a sound measuring apparatus which comprises a container having a peripheral wall and a bottom closure transparent to sound energy, a body of liquid within the container, said body of liquid being partly supported by the bottom closure and having a top surface disposed intermediate the height of the peripheral wall, a tube supported within the container above the body of liquid and having an open lower end disposed near the top surface, mounting means for supporting a sound-generating transducer below the bottom closure and in vibrational contact therewith whereby vibrations generated by said transducer travel upwardly through the body of liquid as sound waves, focusing means for concentrating the sound waves at a focal region located a predetermined distance below the top surface whereby to project a column of said liquid upwardly into the tube to a height proportionate to the output of the transducer, and measuring means for indicating the height of the liquid column within the tube.

In drawings which illustrate preferred embodiments of the invention,

FIG. 1 is a vertical section of a sound measuring apparatus constructed in accordance with one embodiment of the invention, FIG. 2 is a top plan view of the apparatus shown in FIG. 1, FIG. 3 is a vertical section of another embodiment of the sound measuring apparatus, FIG. 4 is a transverse section taken on the line 4—4 of FIG. 3, and FIG. 5 is a schematic view showing, by way of example the FIG. 3 embodiment incorporated in a system for producting chemicals.

The present invention is mainly concerned with ultrasonics or sounds which are too high in frequency to be heard by the human ear. It should be noted, however, that high-frequency sounds within the range of human hearing can be measured by this invention which could be adapted to test sound-producing devices other than those which are equipped with the type of transducer illustrated in the drawings. The following specification will deal mainly with ultrasonic energy but it should be understood that the invention will serve to measure the vibrations of a sound source which is audible to humans.

Referring to FIGS. 1, and 2 of the drawings, the numeral 10 indicates generally a sound measuring apparatus constructed in accordance with a simplified embodiment of the present invention. Apparatus 10 comprises a stand 12 on which a cylindrical container 14 is mounted.

The stand generally indicated at 12 includes a base plate 16 surmounted by cylindrical side wall portions 17 which are circumferentially spaced apart to provide opposing side openings 18. Container 14 fits into an annular recess 19 formed on the wall portion 17 so as to be conveniently locked therein by use of set screws 20.

The container generally indicated at 14 preferably is constructed of a suitable transparent plastic material to provide a peripheral wall 22, a removable cover 23, and a bottom flange 24. A large opening 25 is defined by the inwardly-projecting flange 24 and a bottom closure 26 formed of a suitably thin and flexible membrane is secured as at 27 to the underside of this flange. It will be noted that the bottom closure 26 has a larger diameter than the opening 25 so as to form a pouch below the bottom flange 24 as shown in FIG. 1. The closure 26 is transparent to sound energy, in other words, it will allow sound waves to pass therethrough without impeding those waves to any appreciable extent.

The apparatus 10 is particularly intended to be used to measure the output of sound-generating devices which employ electrically energized transducers to produce vibrational energy. Most such transducers are substantially flat and their associated parts are relatively small and compact which is one reason for selecting the illustrated device as a typical sound generator. In FIG. 1, a typical ultrasonic electrical generator is shown to comprise a therapeutic unit 35 which is required to be tested periodically. This particular unit comprises a head 37 on which a transducer 38 is mounted. A handle 39 on the head carries a conductor cord 40 leading to a high frequency oscillator, not shown. When the oscillator is plugged into a source of alternating current, the transducer is caused to vibrate at a very high or ultrasonic frequency which can be measured by the present instrument.

In order to connect the unit 35 to the instrument 10, the stand 12 is provided with mounting means generally indicated at 43. This mounting means comprises two horizontally opposed bolts 44 which are fitted one to each of the wall portions 17 so that the bolts can be adjusted towards and way from one another. The unit 35 is entered through one of the side openings 18 with the handle 39 horizontal and the head 37 is positioned between the bolt ends, the bolts then being tightened to hold the unit in place with the transducer 38 in contact with the bottom closure 26. Desirably, a thin coating 47 of a suitable gelatin is applied to the top of the transducer before it is installed in the testing position, the gelatin serving to improve the transmission of ultrasonic energy to the closure 26.

The ultrasonic vibrations produced when the transducer 38 is energized will travel upwardly through the container 14 more readily if a suitable propagating medium is provided therein and, for this purpose, the container is partly filled with water or other appropriate liquid generally indicated at 50. The liquid 50 has a top surface designated by the numeral 51. Preferably, the liquid is colored so as to be clearly visible from the exterior of the container of it may have a colored top layer (not shown) for the same purpose.

In this particular embodiment of the invention, the sound waves are concentrated or focused by means generally indicated at 54. As shown in FIG. 1, the focusing means 54 is an acoustic lens 55 which is secured to the container wall 22 a short distance above the bottom closure 26. Lens 55 has a central opening 56 the side edge of which is faced with a parabolic reflector 57. A thin flexible diaphragm 58 is suitably sealed to the top of the lens to close the opening 56, the diaphragm being acoustically transparent as is the bottom closure 26. A centrally disposed conical reflector 59 is secured to the underside of the diaphragm 58. The arrangement of the reflectors 57 and 59 is such that sound waves produced by the unit 35 will be concentrated at a focal region indicated at 60 in FIG. 1. The focal region 60, it will be noticed, if located in the center of the container and a short distance below the surface 51 of the liquid. Thus, the amount of energy concentrated at the focal region is great enough to cause a fountain of the liquid 50 to spurt upwardly as a column which is indicated by the numeral 62 in FIG. 1.

In order to prevent collapse of the liquid column 62, the apparatus 10 is provided with a tube 65. The cover 23 of the container has an integral boss 66 on its underside and the transparent tube 65 is secured to this boss so as to be positioned in the center of the container and directly over the focal region 60. Lower end 67 of the tube is outwardly flared or belled as shown in FIG. 1 and this end is located a short distance below the surface 51 of the liquid. Preferably, the inner surface or bore 68 of the tube is treated with a suitable material such as silicon so that the liquid will not stick to that surface or form beads thereon when projected upwardly as a column. The boss 66 has a vent 69 which normally connects the bore 68 to atmosphere so that the liquid column can rise and fall in the tube.

When the column 62 is projected upwardly into the tube, it will fluctuate slightly due in part to the tendency of the column to move transversely within the tube despite the tube being of a suitably small bore to reduce such fluctuations as much as possible. The column is further guided and stabilized within the tube by a rod 70. This rod is suspended from a small hanger 71 carried by the tube and so as to be centered on the longitudinal axis of the tube with the lowermost end 72 of the rod preferably being located within the belled lower end 67 and only a short distance above the liquid surface 51. Rod 70, in effect, reinforces and steadies the column 62 and thus reduces sideways movement of the column which otherwise might result in an undesirable variation in height.

The column 62, of course, will stand or remain upright in the tube as long as the transducer 38 remains energized and the height of the column can be measured by means generally indicated at 75. As shown in FIG. 1, the measuring means 75 comprises a scale 76 which is marked on the exterior surface of the tube. The linear scale 76 appears on opaque portions 77 of the tube. These transversely spaced portions 77 provide a transparent slot 78 and, through this slot and the transparent wall 22, the column 62 can be seen from the exterior of the container. The scale 76 is calibrated in centimeters or the like to provide a precise measurement of the height of the column, the column height being proportionate to the output of the transducer 38.

Under certain circumstances, it might be advantageous to shut off the therapeutic unit 35 being tested by the present apparatus and to hold the column 62 at is maximum height within the tube. This can be done using valve means generally indicated at 80 in FIGS. 1 and 2. The means 80 comprises a valve disc 82 which is secured to the container cover 23 by a pivot pin 83. A lug 84 is provided on the valve disc opposite the pivot pin whereby the disc can be swung horizontally through a short arc on the cover while remaining an airtight engagement therewith. Disc 82 has a centrally disposed opening 85 which can be placed in register with the vent 68 formed in the boss to extend into the bore 69 of the tube.

The sound measuring apparatus 10 is easily operated to test the efficiency of a device such as the therapeutic unit 35. This unit is simply installed in acoustical contact with the bottom closure 26 by being supported by the mounting means 43. The valve disc 82 is positioned so that the opening 85 is in register with the vent 86 whereupon a switch is closed to energize the transducer 38. Ultrasonic waves produced by the vibrating transducer travel upwardly through the liquid 50 and are focused by the lens 55 at the region 60. The resulting liquid column 62 which is projected upwardly by the concentrated sound energy is supported against sideways collapse by both the tube 65 and the rod 70 so that it is quite a simple matter for an observer to read the height of the column on the scale 76. If desired, the operator of the apparatus shifts the valve disc 82 to move the opening 85 out of register with the vent 86 as shown in FIG. 2 and then shuts off the flow of electric current to the transducer. The column 62 will be suspended in the tube because the tube is no longer vented to atmosphere and the power output reading of the transducer can be taken at a later and more convenient time.

Referring now to FIGS. 3 and 4 of the drawings, the numeral 100 indicates another embodiment of the invention. The sound measuring apparatus 100 is provided with a stand 12 constructed as previously described whereby to support a container 102. This particular container, which is not necessarily transparent, has a cylindrical wall 103 as well as a removable cover 104 and an acoustically transparent bottom closure 105.

The container 102 is fitted with an acoustic lens 108 which has a central opening 109, the parabolic-shaped side 110 of that opening being stepped as shown in FIG. 3. A thin, flexible and acoustically transparent diaphragm 111 is suitably sealed to the top of the lens. The lens is spaced a short distance above the closure 105 to provide a chamber 114 within the container. Access to the chamber 114 is provided by an inlet 115 formed in the side wall 103. A threaded plug 116 fitted to the container wall normally closes the inlet 115.

Above the diaphragm 111, the container 102 has an inwardly projecting flange 120 and this annular flange defines a centrally disposed opening 121. Another sound-transmitting diaphragm 122 is secured to the underside of the horizontal flange 120 to close the opening 121. Thus, a slightly larger chamber 123 is provided within the container above the chamber 114.

The container wall 103 enclosing the chamber 123 is fitted with diametrically opposed sleeve connectors 125 which provide the chamber with ports 126. A pipe section 127 is secured to each of the threaded connectors by means of a coupling nut 128 and these pipe sections form part of a liquid testing circuit which will be described more fully later.

Above the flange 120, the container is fitted with a well 130 having bottom, side, and top walls 131, 132, and 133. A centrally disposed opening 134 formed in the bottom wall of the well is closed by a sound-transmitting diaphragm 135 secured to the underside of that wall. The top wall 133 is perforated as at 136 and is provided with a cone-shaped outlet 137 which projects upwardly concentric about the vertical axis of the container.

A chamber 140 is formed in the container between the well 130 and the flange 120. This chamber has opposing ports 141 provided by threaded sleeve connectors 142 which are fitted to the container wall 103. In FIG. 3, the connectors 142 are shown blanked off by means of caps 143.

The cover 104 of the container has a depending boss 146 in which a vent 147 is formed. A centrally disposed tube 148 is threadedly secured to the boss and this tube has a belled lower end 149 which extends over the outlet 137 of the well as shown in FIG. 3.

Container 102 is provided with valve means 80 for opening and closing the vent 147. Since the means 80 is constructed as previously described, corresponding parts appearing in FIG. 3 are designated by the same reference numerals as in FIGS. 1 and 2.

The sound measuring apparatus 100 is particularly intended for use as a control device in a chemical system and, for that purpose, requires the use of an ultrasonic electrical generator of a known and constant output such as the device indicated generally at 150 in FIG. 3. The device 150 has a head 151 which carries a transducer 152. Preferably, an oscillator 153 is incorporated into the device and a cord 154 is provided to connect the oscillator to a source of alternating current. The previously described mounting means 43 serves to support such a sound-producing device on the stand 12 with the transducer 152 in acoustical contact with the bottom closure 105 of the container.

A body of sound-conducting liquid 160 is provided in the container 102 but, in this embodiment of the invention, the liquid is made up of separated portions which will now be described. One portion 160A completely fills the chamber 114 and is poured therein through the inlet 115 with the container held horizontally. Chamber 123 is completely filled with a liquid portion 160B. The well 130 contains a liquid portion 160C which is poured therein by temporarily removing the top cover 104 of the container so that the well can be filled until top surface 161 of the liquid portion is located just below the top wall 133. By removing one of the caps 143 and again tilting the container horizontally, the chamber 140 is completely filled with a liquid portion 106D.

When the transducer 152 is vibrated, ultrasonic waves will travel upwardly through the liquid 160 and be focused by the lens 108 at a focal region 165. FIG. 3 shows the focal region 165 located in the center of the container and slightly below the surface 161 of the uppermost liquid portion. The focused ultrasonic waves produce a column 168 which is supported or laterally constrained against sideways collapse by the tube 148.

The height of the column 168 is measured by means generally indicated at 180. As shown in FIG. 3, the means 180 comprises an electric circuit 181 which includes a conductor rod 182. This small-diameter rod is mounted on a hanger bracket 183 carried by the tube, the rod extending downwardly through the tube with the lowermost end of the rod terminating just below the surface of the liquid portion 116 and immediately above the focal region 165. Rod 182 is formed of a material which has a high resistance to electricity and the rod has a mechanical function as well, viz., it serves to guide or stabilize the column within the tube.

The means 180 also includes a ring 185 formed of a lower resistance material, this ring being secured to the top of the bottom wall 131 of the well so as to encircle the opening 134. The ring 185 is immersed in the liquid portion 160C and preferably is concentric about the focal region 165. A conductor wire 186 electrically connects the hanger brackets 183 and therefor the rod 182 to a source 187 of alternating current. Another conductor wire 188 electrically connects the ring 185 to an amplifier 189 which is also connected to the power source by a conductor wire 190. The amplifier 189 serves to transmit stepped-up alternating current to a suitable indicator 192. This meter or indicator 192 is calibrated in some suitable manner to give a reading indicative of the height of the column 168 and therefor the intensity of the sound produced by the transducer 152.

It is known that ultrasonics can be used to test a variety of solid materials as well as liquid. The suggestion has been made that ultrasonic waves be caused to pass through a liquid medium containing solid particles or the like so that the measured signal amplitude will provide an indication of the amount of solids in the liquid. The apparatus 100 is particularly well suited for such a measuring task and the pipe section 127 can be connected into a system so that the liquid to be tested can flow through the apparatus and a continous check can be kept on the composition of the liquid. Obviously a reference reading would first have to be obtained and this would be done preferably by filling the chamber 123 with the same liquid which makes up the remainder of the body of liquid 160. The sound producing device 150 is energized briefly to measure the sound transmitting properties of the homogenous liquid 160 and the indicator 192 could then be set to provide the required reference reading.

To operate the apparatus 100 for such a monitoring action, a valve in the system is turned on so that the test liquid flows through the chamber 123 replacing the original liquid portion. Valve means 80 is adjusted to open the vent 147 and the device 150 is then energized whereupon ultrasonic waves travel upwardly through the container 102 and are focused by the lens 108 at the region 165. This concentration of ultrasonic energy results in the formation of the column 168 within the tube and the height of that column is measured by the measuring means 180. The acoustic-impedance mismatch between the test liquid and the remainder of the liquid in the container results in an increased or decreased reading on the indicator 92. Assuming an undesirable increase of foreign particles is detected in the test liquid, the attenuation of ultrasonic energy through the combined liquids increases proportionately and this is recorded on the indicator. Appropriate action can then be taken to adjust the system accordingly.

Referring now to the schematic FIG. 5, the numeral 200 indicates generally a typical system for producing a mixture of chemicals and the sound measuring apparatus 100 can usefully be employed in this system. The system 200 includes a mixing tank 201 in which two ingredients of the mixture are deposited by separate supply pipes 202 and 203. Another mixing tank 205 receives a supply of two different ingredients from supply pipes 206 and 207. A storage tank 210 is provided in the system to receive the mixed ingredients from the other two tanks. For this purpose, the mixing tanks are provided with discharge pipes 211 and 212 which are joined by a solenoid operated valve 214 and a delivery pipe 215 leads from this valve into the storage 210.

The supply tank 201 is provided with bypass pipes 218 and 219 which extend to the chamber 140 within the container 102. In order to connect these bypass pipes to the container, the caps 143 (FIG. 3) are removed and the pipes are coupled directly to the connectors 142 by means of coupling nuts, not shown. Pipe 219 is fitted with a pump 220 and a temperature regulator 221. Thus, a continuous sample of the two ingredients which are mixed within the tank can be circulated through the testing chamber 140, of the apparatus.

The second tank 205 is connected by bypass pipes 224 and 225 to the chamber 123 with the coupling nuts 128 joining the pipes to the sleeve couplings 125. A pump 226 and a temperature regulator 227 are provided in the pipe 225 whereby a sample of the two ingredients mixed within the testing chamber 123 can be brought to an appropriate temperature and be continuously circulated through the apparatus.

The previously described measuring means 180 of the apparatus 100 is connected by conductors 230 and 231 to the solenoid operated valve 214. The arrangement is such that a valve will open when a predetermined measurement registers on the meter 192.

The apparatus 200 operates to monitor the two batches of mixed ingredients. For example, if there is a density change in one or both of the batches, the ultrasonic waves will be attenuated or reflected to a greater or lesser degree which is registered on the indicator 92. When the reading is within a predetermined range, the valve 24 opens and the contents of the two mixing tanks are dumped into the storage tank. Preferably, the amplifier 189 is adjusted so as to give a minimum reading on the indicator 192 at the beginning of a chemical reaction. The final reactants in the test liquids result in a decrease in attenuation whereupon the indicator would indicate a maximum reading and a voltage in the circuit associated with the measuring means would be sufficient to trigger the solenoid valve 214 and the storage tank 210 would receive the contents of the two mixing tanks. In between the minimum and maximum reading, the indicator could be marked to show as a percentage the degree to which the chemical reaction in the system has been completed rather than being graduated to show sound level intensity.

From the foregoing description, it will be apparent the invention provides an extremely simple and therefore inexpensive instrument for measuring sound. The device does not demand extremely careful handling and can be operated by other than highly-skilled technicians. The embodiments of the invention which lend themselves to process control applications are very versatile and can be used to measure the constituents in a liquid other than solid particulate matter. This is possible because the transmission of sound through a liquid is affected by the concentration of the constituents in the solution. Temperature also effects the sound transmission hence the need to control the temperature of the liquid as measurements are taken. Thus, the present invention can form an essential part of a number of chemical-producing as well as other systems to provide continuous analysis and automatic control.

I claim:
1. Apparatus for measuring the intensity of sound comprising;
   a container having a peripheral wall and a bottom closure transparent to sound energy,
   a body of liquid within the container, said body of liquid being partly supported by the bottom closure and having a top surface disposed intermediate the height of the peripheral wall,
   a tube supported within the container above the body of liquid and having an open lower end disposed near the top surface,
   mounting means for supporting a sound-generating transducer below the bottom closure and in vibrational contact therewith whereby vibrations generated by said transducer travel upwardly through the body of liquid as sound waves,
   focusing means for concentrating the sound waves at a focal region located a predetermined distance below the top surface whereby to project a column of said liquid upwardly into the tube to a height proportionate to the output of the transducer, and
   measuring means for indicating the height of the liquid column within the tube.

2. Apparatus as claimed in claim 1, and including a rod supported concentrically within the tube and cooperating therewith to additionally support the liquid column.

3. Apparatus as claimed in claim 1, in which said container has a vent opening normally connecting the bore of the tube to atmosphere, and valve means on the container operable to selectively close the vent and seal the bore against atmospheric pressure.

4. Apparatus as claimed in claim 1, and including a well supported within the container to enclose the focal region, said well containing a column-forming portion of the body of liquid.

5. Apparatus as claimed in claim 4, in which said measuring means comprises an electric circuit connected to a source of power and including an indicating meter, a conductor rod supported concentrically within the tube, a contact within the well, said column-forming portion of the body of liquid being a conductor capable of electrically connecting the contact to the conductor rod when said liquid column is projected upwardly into the tube, and an amplifier connecting by the electric circuit to the indicating meter whereby said meter is energized to provide a reading indicative of the height of the column.

6. Apparatus as claimed in claim 1, in which said container has transverse members transparent to sound energy arranged to exclude a portion of the body of liquid and provide a testing chamber below the focal region, and conduit means connected to the container for delivering a test liquid to the testing chamber.

7. Apparatus for measuring the intensity of sound comprising:
- a container having a peripheral wall and a flexible bottom closure,
- first and second members transparent to sound energy extending across the container to provide a testing chamber therein,
- a conduit means for flowing a test liquid through the testing chamber,
- a body of liquid partly filling the remainder of the container above the flexible bottom closure and having a top surface intermediate the height of the peripheral wall,
- a well within the container having a bottom member transparent to sound energy in vibrational contact with the top surface, and a separate liquid contained within the well,
- a tube supported within the container above the well and having an open end near the separate liquid,
- an acoustic generator including means for activating said generator to produce ultrasonic waves of a known intensity,
- mounting means for supporting the acoustic generator below the flexible bottom closure and in vibrational contact therewith whereby to cause ultrasonic waves to travel upwardly through the body of liquid and the test liquid,
- focusing means for concentrating the sound waves at a focal region immersed in the separate liquid whereby to project a column of said liquid upwardly into the tube, and
- measuring means for indicating the height of the projected column.

8. A method of measuring the intensity of sound comprising the steps of
- containing a body of liquid,
- causing sound waves to travel upwardly through the body of liquid,
- concentrating the sound waves at a point of maximum force located below and in close proximity to the surface of the body of liquid whereby to project a column of said liquid above said surface,
- constraining the projected liquid column laterally against sideways collapse, and
- measuring the height of the projected liquid column on a scale calibrated to provide an indication of the intensity of the sound waves.

9. The method as claimed in claim 8, and including a further step of flowing a test liquid transversely through the body of liquid whereby the resulting measurement is indicative of the composition of said test liquid.

10. The method as claimed in claim 9, and including a further step of flowing a second test liquid transversely through the body of contained liquid in vertically spaced relation to the first mentioned test liquid to influence the measurement of the height of the column and thereby provide usable information based on a comparison between the compositions of the first and second test liquids.

* * * * *